United States Patent
Litvak et al.

(10) Patent No.: US 12,220,596 B2
(45) Date of Patent: *Feb. 11, 2025

(54) SYSTEMS AND METHODS FOR PROVIDING ELECTROMAGNETIC THERAPY TO AN IMPLANTABLE DEVICE RECIPIENT

(71) Applicant: Advanced Bionics AG, Staefa (CH)

(72) Inventors: Leonid M. Litvak, Los Angeles, CA (US); R. Tissa Karunasiri, Valencia, CA (US); Kanthaiah Koka, Valencia, CA (US); Smita S. Agrawal, Stevenson Ranch, CA (US)

(73) Assignee: Advanced Bionics AG, Staefa (CH)

( * ) Notice: Subject to any disclaimer, the term of this patent is extended or adjusted under 35 U.S.C. 154(b) by 221 days.

This patent is subject to a terminal disclaimer.

(21) Appl. No.: 18/074,885

(22) Filed: Dec. 5, 2022

(65) Prior Publication Data
US 2023/0108415 A1    Apr. 6, 2023

Related U.S. Application Data

(62) Division of application No. 16/878,007, filed on May 19, 2020, now Pat. No. 11,554,268.

(51) Int. Cl.
| | | |
|---|---|---|
| *A61N 2/02* | (2006.01) | |
| *A61N 2/00* | (2006.01) | |
| *H04R 25/00* | (2006.01) | |
| *A61N 1/36* | (2006.01) | |
| *A61N 1/362* | (2006.01) | |

(52) U.S. Cl.
CPC .............. *A61N 2/008* (2013.01); *A61N 2/02* (2013.01); *A61N 1/36038* (2017.08); *A61N 1/362* (2013.01); *H04R 25/00* (2013.01)

(58) Field of Classification Search
None
See application file for complete search history.

(56) References Cited

U.S. PATENT DOCUMENTS

| 7,344,491 B1 | 3/2008 | Seeney et al. |
| 7,520,849 B1 | 4/2009 | Simon |
| 2012/0296155 A1* | 11/2012 | Ball ............... A61N 1/3718 607/57 |
| 2013/0345767 A1 | 12/2013 | Menzl et al. |
| 2014/0221726 A1 | 8/2014 | Pilla et al. |
| 2019/0290925 A1* | 9/2019 | Gellman ............. A61N 2/004 |

OTHER PUBLICATIONS

Pilla, et al., "Nonthermal electromagnetic fields: From first messenger to therapeutic applications", (2013) Electromagnetic Biology and Medicine, 32:2, 123-136, DOI: 10.3109/15368378.2013.776335.

* cited by examiner

*Primary Examiner* — Thaddeus B Cox
(74) *Attorney, Agent, or Firm* — ALG Intellectual Property, LLC

(57) ABSTRACT

An illustrative system includes a coil configured to be positioned over a wound on a body and held in place on the body by a magnet implanted within the body; and a controller communicatively coupled to the coil, the controller configured to apply therapeutic electromagnetic pulses by way of the coil to the wound. Other systems and methods for providing therapeutic electromagnetic pulses to a recipient are also disclosed.

20 Claims, 7 Drawing Sheets

SYSTEMS AND METHODS FOR PROVIDING ELECTROMAGNETIC THERAPY TO AN IMPLANTABLE DEVICE RECIPIENT

RELATED APPLICATIONS

This application is a divisional application of U.S. patent application Ser. No. 16/878,007, filed May 19, 2020 and issued as U.S. Pat. No. 11,554,268, which is hereby incorporated by reference in its entirety.

BACKGROUND INFORMATION

To implant a cochlear implant and electrode lead within a recipient, a surgeon conventionally makes an incision within the recipient's head near an ear of the recipient. The resulting wound takes time to heal, during which time the recipient may experience discomfort and/or pain at the wound site.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Systems and methods for providing electromagnetic therapy to an implantable device recipient are described herein. For example, a system may include a coil configured to be positioned over a wound on a head of a recipient, the wound created during an implant procedure in which a cochlear implant is implanted within the recipient. The system may further include a controller communicatively coupled to the coil. The controller may be configured to selectively operate in a therapeutic mode in which the controller applies therapeutic electromagnetic pulses by way of the coil to the wound. The therapeutic electromagnetic pulses may be configured to alleviate pain felt by the recipient while the wound heals. The controller may be further configured to selectively operate in a cochlear implant interface mode in which the controller communicates by way of the coil with the cochlear implant.

In another exemplary configuration, a system may include a coil configured to be positioned over a wound on a body and held in place on the body by a magnet implanted within the body. The system may further include a controller communicatively coupled to the coil, the controller configured to apply therapeutic electromagnetic pulses by way of the coil to the wound. In this configuration, the magnet may be included in an implantable assembly that also includes an implantable device (e.g., an implantable stimulator, a cochlear implant, and/or any other type of implantable medical device). The controller may be configured to communicate with the implantable device by way of the coil.

The systems and methods described herein may advantageously provide various benefits to an implantable device recipient. For example, the systems and methods described herein may use the same components (e.g., a headpiece including a coil) to both aid in the healing process of a wound created during a cochlear implant insertion procedure (or any other type of implantable device insertion procedure) and communicate with the cochlear implant after the cochlear implant has been implanted within the recipient. The electromagnetic therapy provided by the systems and methods described herein may be used pre-operatively (e.g., to condition or otherwise prepare an insertion site on the head of the recipient prior to surgery), intra-operatively (e.g., to reduce inflammation, pain, or other effects of the surgery), and/or post-operatively (e.g., to reduce pain and/or accelerate the rate of healing of the wound created during the surgery). These and other advantages and benefits of the systems and methods described herein will be made apparent herein.

Figure 1:
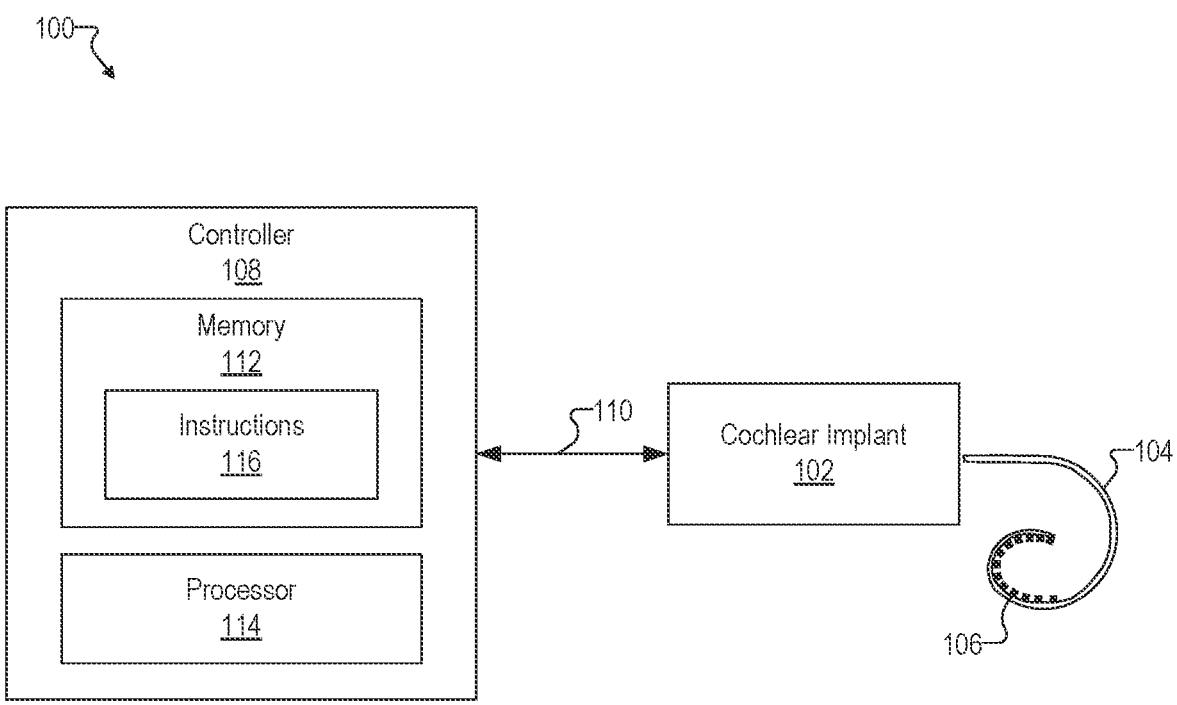
FIG. 1 illustrates an exemplary cochlear implant system configured to provide therapeutic electromagnetic pulses according to principles described herein.

FIG. 1 illustrates an exemplary cochlear implant system 100 configured to be used by a recipient. As shown, cochlear implant system 100 includes a cochlear implant 102, an electrode lead 104 physically coupled to cochlear implant 102 and having an array of electrodes 106, and a controller 108 configured to be communicatively coupled to cochlear implant 102 by way of a communication link 110.

The cochlear implant system 100 shown in FIG. 1 is unilateral (i.e., associated with only one ear of the recipient). Alternatively, a bilateral configuration of cochlear implant system 100 may include separate cochlear implants and electrode leads for each ear of the recipient. In the bilateral configuration, controller 108 may be implemented by a single controller configured to interface with both cochlear implants or by two separate controllers each configured to interface with a different one of the cochlear implants.

Cochlear implant 102 may be implemented by any suitable type of implantable stimulator. For example, cochlear implant 102 may be implemented by an implantable cochlear stimulator. Additionally or alternatively, cochlear implant 102 may be implemented by a brainstem implant and/or any other type of device that may be implanted within the recipient and configured to apply electrical stimulation to one or more stimulation sites located along an auditory pathway of the recipient.

In some examples, cochlear implant 102 may be configured to generate electrical stimulation representative of an audio signal processed by controller 108 in accordance with one or more stimulation parameters transmitted to cochlear implant 102 by controller 108. Cochlear implant 102 may be further configured to apply the electrical stimulation to one or more stimulation sites (e.g., one or more intracochlear locations) within the recipient by way of one or more electrodes 106 on electrode lead 104. In some examples, cochlear implant 102 may include a plurality of independent current sources each associated with a channel defined by one or more of electrodes 106. In this manner, different stimulation current levels may be applied to multiple stimulation sites simultaneously by way of multiple electrodes 106.

Cochlear implant 102 may additionally or alternatively be configured to generate, store, and/or transmit data. For example, cochlear implant may use one or more electrodes 106 to record one or more signals (e.g., one or more voltages, impedances, evoked responses within the recipient, and/or other measurements) and transmit, by way of communication link 110, data representative of the one or more signals to controller 108. In some examples, this data is referred to as back telemetry data.

Electrode lead 104 may be implemented in any suitable manner. For example, a distal portion of electrode lead 104 may be pre-curved such that electrode lead 104 conforms with the helical shape of the cochlea after being implanted. Electrode lead 104 may alternatively be naturally straight or of any other suitable configuration.

In some examples, electrode lead 104 includes a plurality of wires (e.g., within an outer sheath) that conductively couple electrodes 106 to one or more current sources within cochlear implant 102. For example, if there are n electrodes 106 on electrode lead 104 and n current sources within cochlear implant 102, there may be n separate wires within electrode lead 104 that are configured to conductively connect each electrode 106 to a different one of the n current sources. Exemplary values for n are 8, 12, 16, or any other suitable number.

Electrodes 106 are located on at least a distal portion of electrode lead 104. In this configuration, after the distal portion of electrode lead 104 is inserted into the cochlea, electrical stimulation may be applied by way of one or more of electrodes 106 to one or more intracochlear locations. One or more other electrodes (e.g., including a ground electrode, not explicitly shown) may also be disposed on other parts of electrode lead 104 (e.g., on a proximal portion of electrode lead 104) to, for example, provide a current return path for stimulation current applied by electrodes 106 and to remain external to the cochlea after the distal portion of electrode lead 104 is inserted into the cochlea. Additionally or alternatively, a housing of cochlear implant 102 may serve as a ground electrode for stimulation current applied by electrodes 106.

Controller 108 may be configured to interface with (e.g., control and/or receive data from) cochlear implant 102. For example, controller 108 may transmit commands (e.g., stimulation parameters and/or other types of operating parameters in the form of data words included in a forward telemetry sequence) to cochlear implant 102 by way of communication link 110. Controller 108 may additionally or alternatively provide operating power to cochlear implant 102 by transmitting one or more power signals to cochlear implant 102 by way of communication link 110. Controller 108 may additionally or alternatively receive data from cochlear implant 102 by way of communication link 110.

Communication link 110 may be implemented by any suitable number of wired and/or wireless bidirectional and/or unidirectional links.

As shown, controller 108 includes a memory 112 and a processor 114 configured to be selectively and communicatively coupled to one another. In some examples, memory 112 and processor 114 may be distributed between multiple devices and/or multiple locations as may serve a particular implementation.

Memory 112 may be implemented by any suitable non-transitory computer-readable medium and/or non-transitory processor-readable medium, such as any combination of non-volatile storage media and/or volatile storage media. Exemplary non-volatile storage media include, but are not limited to, read-only memory, flash memory, a solid-state drive, a magnetic storage device (e.g., a hard drive), ferroelectric random-access memory ("RAM"), and an optical disc. Exemplary volatile storage media include, but are not limited to, RAM (e.g., dynamic RAM).

Memory 112 may maintain (e.g., store) executable data used by processor 114 to perform one or more of the operations described herein. For example, memory 112 may store instructions 116 that may be executed by processor 114 to perform any of the operations described herein. Instructions 116 may be implemented by any suitable application, program (e.g., sound processing program), software, code, and/or other executable data instance. Memory 112 may also maintain any data received, generated, managed, used, and/or transmitted by processor 114.

Processor 114 may be configured to perform (e.g., execute instructions 116 stored in memory 112 to perform) various operations with respect to cochlear implant 102.

To illustrate, processor 114 may be configured to control an operation of cochlear implant 102. For example, processor 114 may receive an audio signal (e.g., by way of a microphone communicatively coupled to controller 108, a wireless interface (e.g., a Bluetooth interface), and/or a wired interface (e.g., an auxiliary input port)). Processor 114 may process the audio signal in accordance with a sound processing program (e.g., a sound processing program stored in memory 112) to generate appropriate stimulation parameters. Processor 114 may then transmit the stimulation parameters to cochlear implant 102 to direct cochlear implant 102 to apply electrical stimulation representative of the audio signal to the recipient.

In some implementations, processor 114 may also be configured to apply acoustic stimulation to the recipient. For example, a receiver (also referred to as a loudspeaker) may be optionally coupled to controller 108. In this configuration, processor 114 may deliver acoustic stimulation to the recipient by way of the receiver. The acoustic stimulation may be representative of an audio signal (e.g., an amplified version of the audio signal), configured to elicit an evoked response within the recipient, and/or otherwise configured. In configurations in which processor 114 is configured to both deliver acoustic stimulation to the recipient and direct cochlear implant 102 to apply electrical stimulation to the recipient, cochlear implant system 100 may be referred to as a bimodal hearing system and/or any other suitable term.

Processor 114 may be additionally or alternatively configured to receive and process data generated by cochlear implant 102. For example, processor 114 may receive data representative of a signal recorded by cochlear implant 102 using one or more electrodes 106 and, based on the data, adjust one or more operating parameters of controller 108. Additionally or alternatively, processor 114 may use the data to perform one or more diagnostic operations with respect to cochlear implant 102 and/or the recipient.

Other operations may be performed by processor 114 as may serve a particular implementation. In the description provided herein, any references to operations performed by controller 108 and/or any implementation thereof may be understood to be performed by processor 114 based on instructions 116 stored in memory 112.

Figure 2:
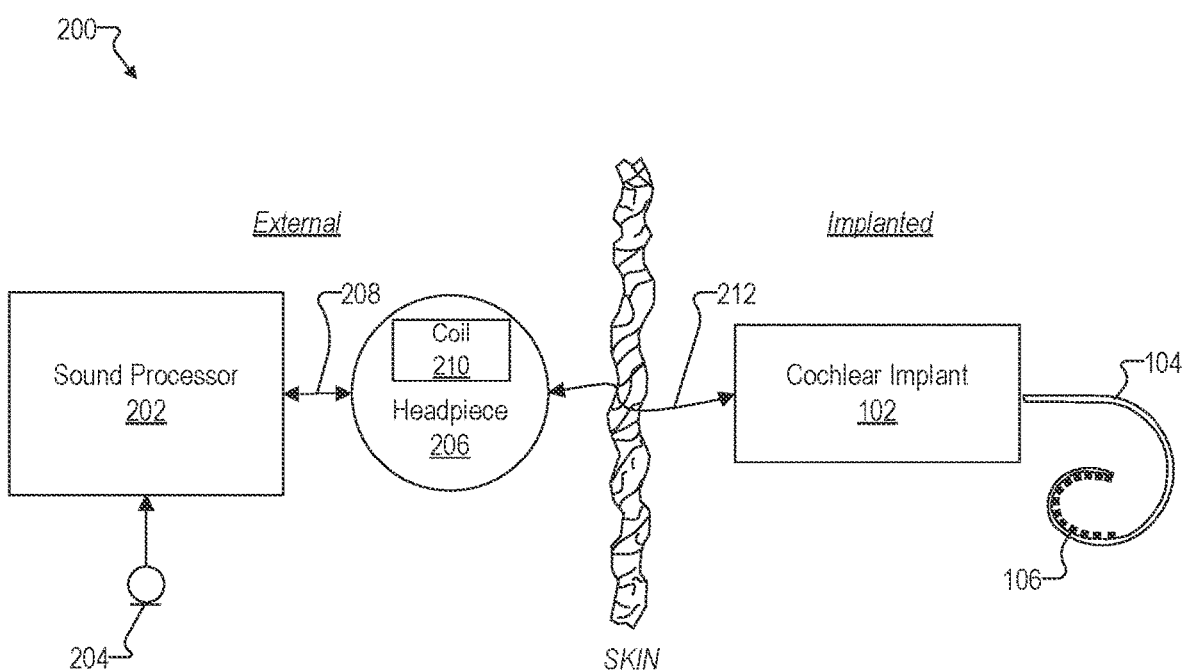
FIG. 2 shows an exemplary configuration of the cochlear implant system of FIG. 1 according to principles described herein.

Controller 108 may be implemented by one or more devices configured to interface with cochlear implant 102. To illustrate, FIG. 2 shows an exemplary configuration 200 of cochlear implant system 100 in which controller 108 is implemented by a sound processor 202 configured to be located external to the recipient. In configuration 200, sound processor 202 is communicatively coupled to a microphone 204 and to a headpiece 206 that are both configured to be located external to the recipient.

Sound processor 202 may be implemented by any suitable device that may be worn or carried by the recipient. For example, sound processor 202 may be implemented by a behind-the-ear ("BTE") unit configured to be worn behind and/or on top of an ear of the recipient. Additionally or alternatively, sound processor 202 may be implemented by an off-the-ear unit (also referred to as a body worn device) configured to be worn or carried by the recipient away from the ear. Additionally or alternatively, at least a portion of sound processor 202 is implemented by circuitry within headpiece 206.

Microphone 204 is configured to detect one or more audio signals (e.g., that include speech and/or any other type of sound) in an environment of the recipient. Microphone 204 may be implemented in any suitable manner. For example, microphone 204 may be implemented by a microphone that is configured to be placed within the concha of the ear near the entrance to the ear canal, such as a T-MIC™ microphone from Advanced Bionics. Such a microphone may be held within the concha of the ear near the entrance of the ear canal during normal operation by a boom or stalk that is attached to an ear hook configured to be selectively attached to sound processor 202. Additionally or alternatively, microphone 204 may be implemented by one or more microphones in or on headpiece 206, one or more microphones in or on a housing of sound processor 202, one or more beam-forming microphones, and/or any other suitable microphone as may serve a particular implementation.

Headpiece 206 may be selectively and communicatively coupled to sound processor 202 by way of a communication link 208 (e.g., a cable or any other suitable wired or wireless communication link), which may be implemented in any suitable manner. As shown, headpiece 206 includes a coil 210, which may be implemented by any suitable antenna, electromagnetic field generator, and/or wireless communication component as may serve a particular implementation. As described herein, while sound processor 202 (or any other implementation of controller 108) operates in a therapeutic mode, coil 210 may be used to apply therapeutic electromagnetic pulses to a wound. While sound processor 202 operates in a cochlear implant interface mode, coil 210 may be used as an external antenna configured to facilitate selective wireless coupling of sound processor 202 to cochlear implant 102. In this configuration, headpiece 206 may be affixed to the recipient's head and positioned such that the coil 210 is communicatively coupled to a corresponding implantable antenna (which may also be implemented by a coil and/or one or more wireless communication components) included within or otherwise connected to cochlear implant 102. In this manner, stimulation parameters and/or power signals may be wirelessly and transcutaneously transmitted between sound processor 202 and cochlear implant 102 by way of a wireless communication link 212.

In configuration 200, sound processor 202 may receive an audio signal detected by microphone 204 by receiving a signal (e.g., an electrical signal) representative of the audio signal from microphone 204. Sound processor 202 may additionally or alternatively receive the audio signal by way of any other suitable interface as described herein. Sound processor 202 may process the audio signal in any of the ways described herein and transmit, by way of headpiece 206, stimulation parameters to cochlear implant 102 to direct cochlear implant 102 to apply electrical stimulation representative of the audio signal to the recipient.

Figure 3:
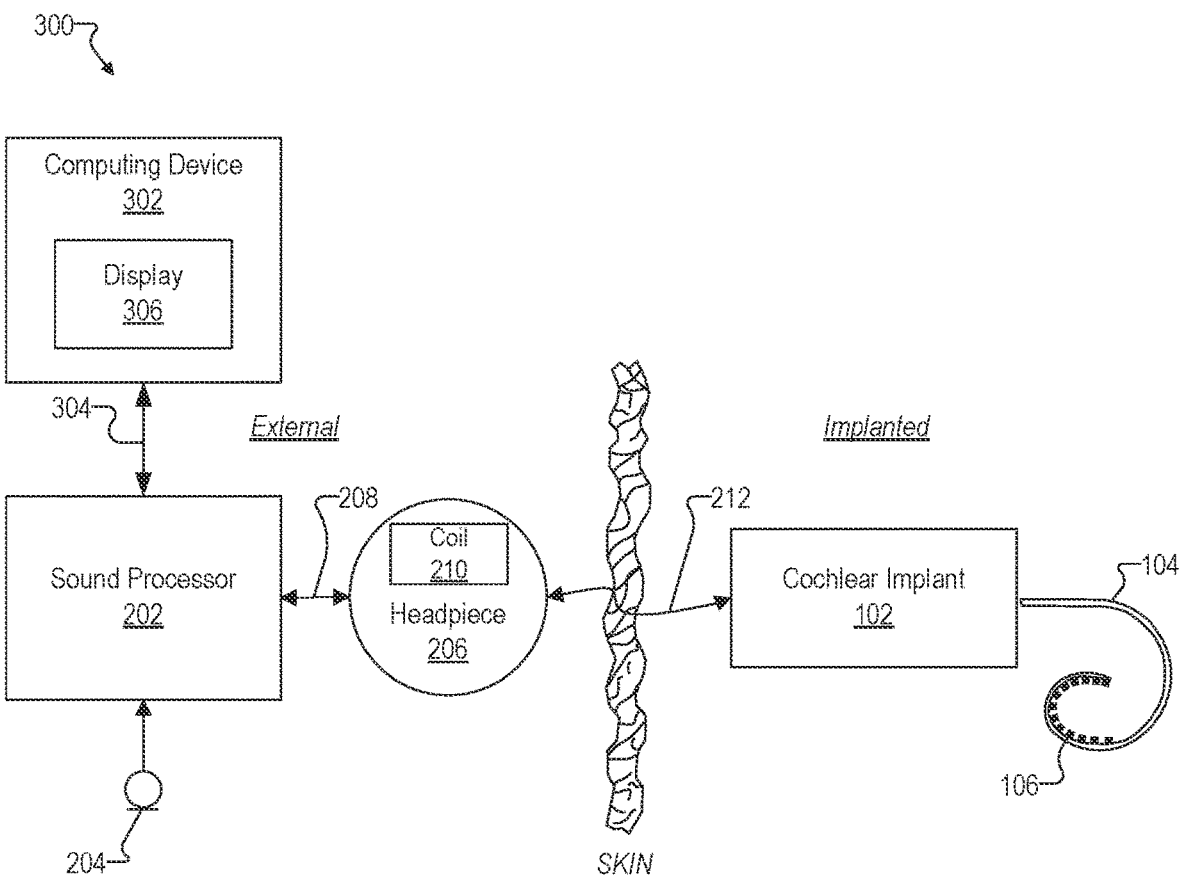
FIG. 3 shows another exemplary configuration of the cochlear implant system of FIG. 1 according to principles described herein.

FIG. 3 shows an exemplary configuration 300 of cochlear implant system 100 in which controller 108 is implemented by a combination of sound processor 202 and a computing device 302 configured to communicatively couple to sound processor 202 by way of a communication link 304, which may be implemented by any suitable wired or wireless communication link.

Computing device 302 may be implemented by any suitable combination of hardware and software. To illustrate, computing device 302 may be implemented by a mobile device (e.g., a mobile phone, a laptop, a tablet computer, etc.), a desktop computer, and/or any other suitable computing device as may serve a particular implementation. As an example, computing device 302 may be implemented by a mobile device configured to execute an application (e.g., a "mobile app") that may be used by a user (e.g., the recipient, a clinician, and/or any other user) to control one or more settings of sound processor 202 and/or cochlear implant 102 and/or perform one or more operations (e.g., diagnostic operations) with respect to data generated by sound processor 202 and/or cochlear implant 102.

In some examples, computing device 302 may be configured to control an operation of cochlear implant 102 by transmitting one or more commands to cochlear implant 102 by way of sound processor 202. Likewise, computing device 302 may be configured to receive data generated by cochlear implant 102 by way of sound processor 202. Alternatively, computing device 302 may interface with (e.g., control and/or receive data from) cochlear implant 102 directly by way of a wireless communication link between computing device 302 and cochlear implant 102. In some implementations in which computing device 302 interfaces directly with cochlear implant 102, sound processor 202 may or may not be included in cochlear implant system 100.

Computing device 302 is shown as having an integrated display 306. Display 306 may be implemented by a display screen, for example, and may be configured to display content generated by computing device 302. Additionally or alternatively, computing device 302 may be communicatively coupled to an external display device (not shown) configured to display the content generated by computing device 302.

In some examples, computing device 302 represents a fitting device configured to be selectively used (e.g., by a clinician) to fit sound processor 202 and/or cochlear implant 102 to the recipient. In these examples, computing device 302 may be configured to execute a fitting program configured to set one or more operating parameters of sound processor 202 and/or cochlear implant 102 to values that are optimized for the recipient. As such, in these examples, computing device 302 may not be considered to be part of cochlear implant system 100. Instead, computing device 302 may be considered to be separate from cochlear implant system 100 such that computing device 302 may be selectively coupled to cochlear implant system 100 when it is desired to fit sound processor 202 and/or cochlear implant 102 to the recipient.

Figure 4:
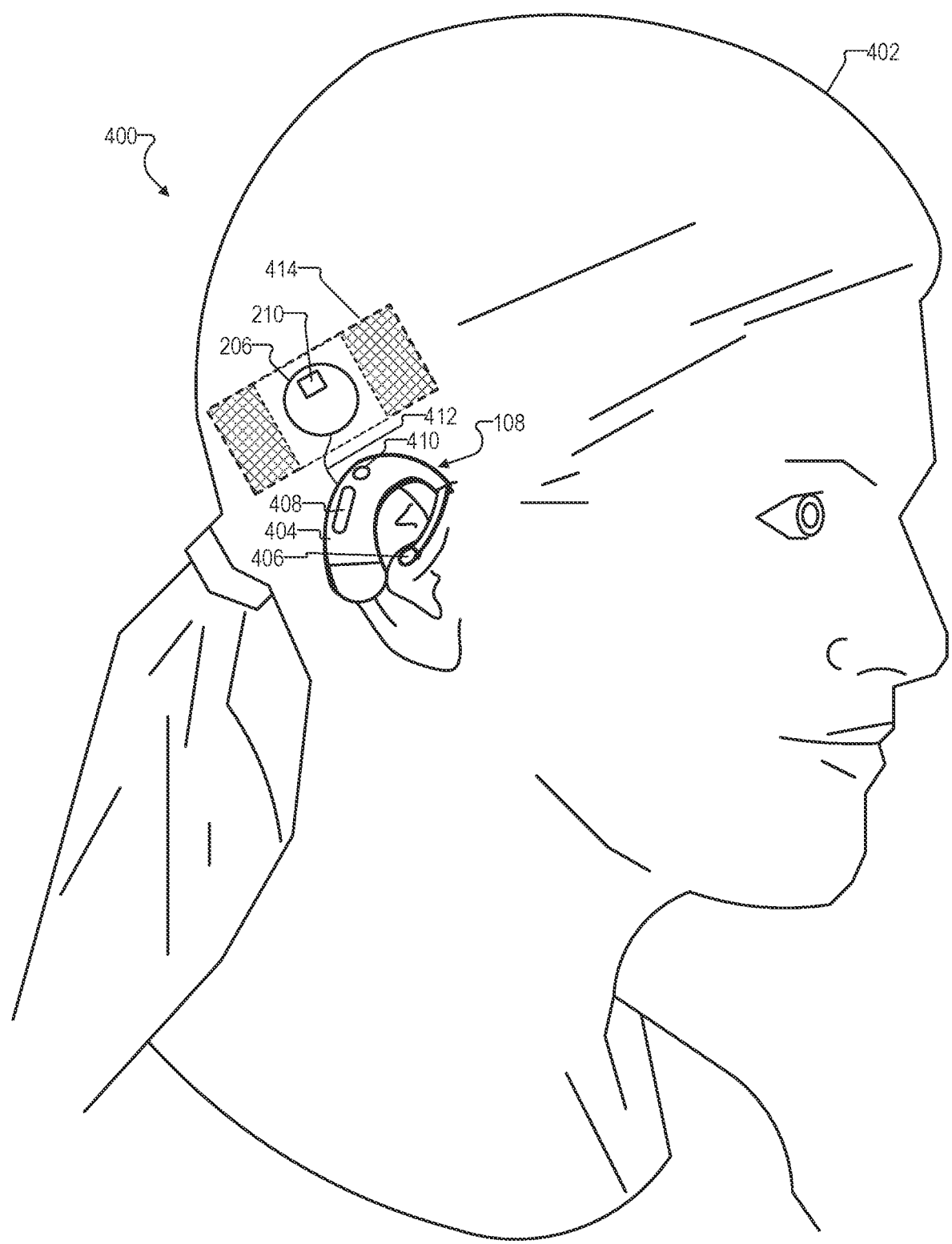
FIG. 4 illustrates an exemplary configuration in which a headpiece is included within a wound covering according to principles described herein.

FIG. 4 illustrates an exemplary configuration 400 in which controller 108 is implemented by a BTE unit that is worn by a recipient 402. As shown, controller 108 includes a housing 404 that is configured to be worn behind and/or on top of an ear of recipient 402. Housing 404 may house various components of controller 108 and is connected to a microphone 406 that is positioned at an ear canal entrance of recipient 402. As shown, a user input button 408 and a status indicator 410 may be located on housing 404.

As shown, headpiece 206, which includes coil 210, is coupled to controller 108 by way of a cable 412. In some examples, headpiece 206 is removably coupled to housing 404 In certain examples, headpiece 206 may be configured to be magnetically held in place on the head of recipient 402 by a magnet of the cochlear implant.

In the configuration shown in FIG. 4, headpiece 206 is positioned in or over a wound covering 414 (e.g., an adhesive bandage) that covers a wound created during an implant procedure in which cochlear implant 102 and/or electrode lead 104 are implanted within recipient 402. Wound covering 414 may be placed over the wound for a period of time following an implant procedure. As described herein, in this configuration, controller 108 may be configured to operate in a therapeutic mode. When the wound has sufficiently healed and it is desired for controller 108 to operate in the cochlear implant interface mode, wound covering 414 may be removed and headpiece 206 may be placed directly on the head of the recipient 402. Headpiece 206 may alternatively be located in an article of clothing or placed directly on the head over the wound while controller 108 operates in the therapeutic mode.

Figure 5:
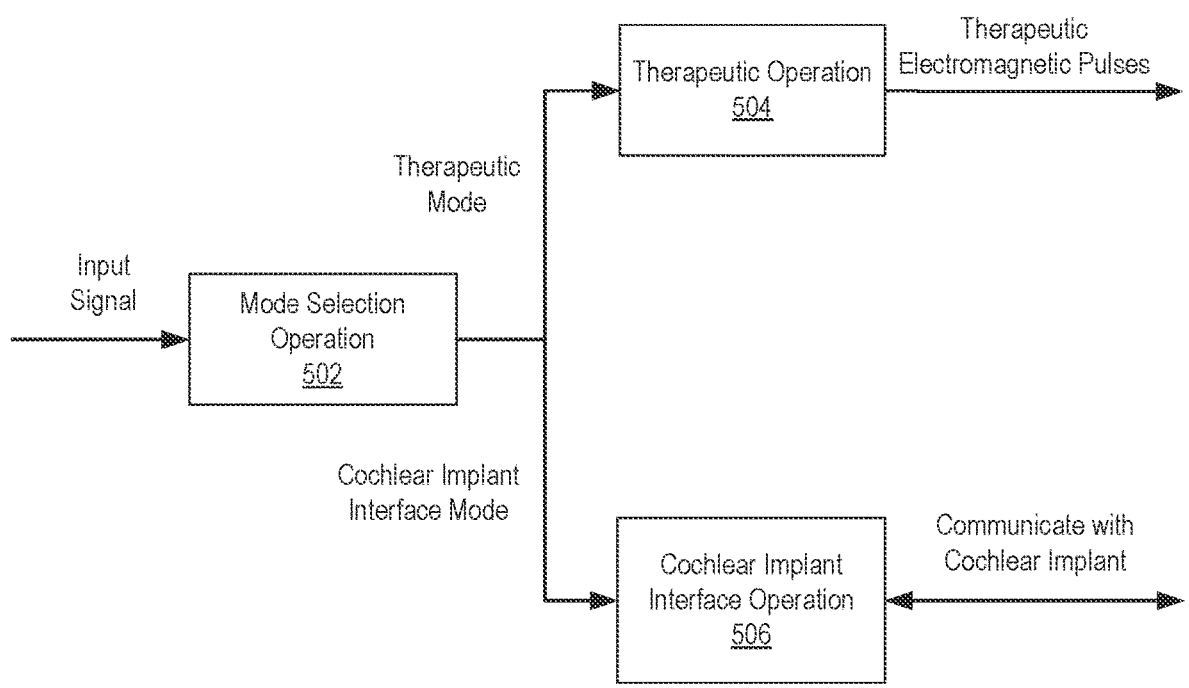
FIG. 5 illustrates exemplary operations that may be performed by a controller according to principles described herein.

As described herein, controller 108 may be configured to selectively operate in at least two different modes. To illustrate, FIG. 5 shows exemplary operations that may be performed by controller 108.

As shown, an input signal is received by a mode selection operation 502. Mode selection operation 502 may be configured to select a mode of operation for controller 108, such as between a therapeutic mode and a cochlear implant interface mode, based on the input signal.

In some examples, the input signal is provided by a user (e.g., the cochlear implant recipient). For example, the user may provide the input signal by pressing user input button 408 (which may be a volume selection button or any other suitable button on housing 404), selecting an option in an application (e.g., a mobile application) associated with controller 108, etc.

Alternatively, the input signal may be provided by a component of the cochlear implant system. For example, the input signal may be a feedback signal representative of a diagnostic operation configured to automatically determine when a particular mode of operation is needed.

As shown, if mode selection operation 502 selects a therapeutic mode, a therapeutic operation 504 outputs therapeutic electromagnetic pulses by way of coil 210. The therapeutic electromagnetic pulses may be output by way of coil 210 in accordance with a therapeutic program stored in memory of controller 108 or otherwise accessed by controller 108.

The therapeutic program may specify various parameters of the therapeutic electromagnetic pulses output by therapeutic program selection operation 504. Exemplary parameters include, but are not limited to, an amplitude, a modulation depth, a pulse frequency, a pulse duration, and/or any other suitable parameter of the therapeutic electromagnetic pulses. For example, a therapeutic program may specify the following parameters: electromagnetic pulses configured to be applied 20-30 minutes per hour at a pulse frequency between 1000 Hz-5000 Hz and having pulse duration between 100 microseconds-2 milliseconds. Other therapeutic program parameter values may be used as may serve a particular implementation.

In some examples, a user may provide user input representative of a command to adjust a value for a parameter specified by a particular therapeutic program. The user input may be provided in any of the ways described herein. In response to the user input, controller 108 may adjust the value of the parameter. In this way, the user may adjust a parameter value to a value that is most efficacious for the recipient.

In some examples, controller 108 may determine a placement context of coil 210 and, in response, select the therapeutic program based on the determined placement context of coil 210. For example, controller 108 may receive user input indicating the placement context of a coil (e.g., that the coil is placed directly over the wound, over or within a wound covering, etc.). Based on this input, controller 108 may select a particular therapeutic program and/or adjust one or more parameters (e.g., power levels) of a therapeutic program.

Alternatively, if mode selection operation 502 selects a cochlear implant interface mode, a cochlear implant interface operation 506 communicates with the cochlear implant by way of coil 210. For example, in this mode, cochlear implant interface operation 506 may include receiving an audio signal and wirelessly transmit a command to the cochlear implant, by way of coil 210, to direct the cochlear implant to apply electrical stimulation representative of the audio signal. In this mode, cochlear implant interface operation 506 may additionally or alternatively include wirelessly receiving data from the cochlear implant by way of coil 210. For example, controller 108 may receive data indicative of changes in electrode impedances over time and/or any other type of back-telemetry data. Controller 108 may use this data to guide a manner in which controller 108 operates in the cochlear implant interface mode. For example, during a time period following an implant procedure, controller 108 may initially only receive data from the cochlear implant (and not transmit data to the cochlear implant directing the cochlear implant to apply electrical stimulation representative of audio signals to the recipient). As the recipient heals, a change in electrode impedance measurements may indicate that the recipient is ready to begin receiving stimulation representative of audio signals. Controller 108 may accordingly begin directing the cochlear implant to apply electrical stimulation representative of audio signals.

In some examples, controller 108 may be configured to concurrently operate in both the therapeutic mode and the cochlear implant interface mode. In these examples, controller 108 may concurrently apply therapeutic electromagnetic pulses and communicate with the cochlear implant. This concurrent operation may be beneficial in various post-operative scenarios.

In some examples, controller 108 may provide a visible and/or audible indication of a particular mode in which controller 108 is operating. For example, status indicator 410 may be implemented by a light emitting diode configured to indicate (e.g., by a particular color, blinking sequence, and/or any other suitable indication) when controller 108 is operating in a particular mode (e.g., a therapeutic mode or a cochlear implant interface mode). Status indicator 410 may be alternatively implemented in any suitable manner.

Figure 6:
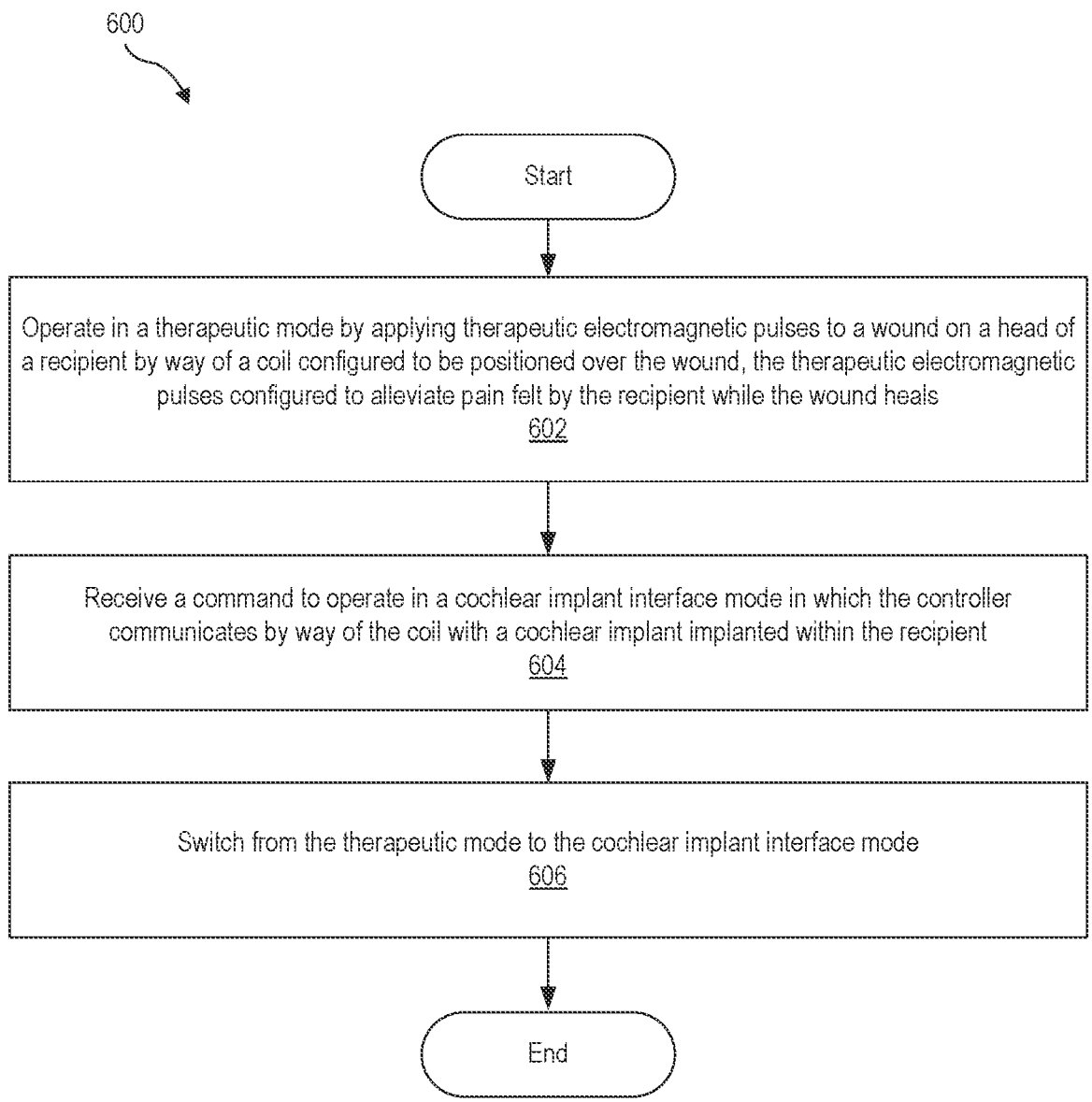
FIG. 6 illustrates an exemplary method according to principles described herein.

FIG. 6 illustrates an exemplary method 600 according to principles described herein. The operations shown in FIG. 6 may be performed by cochlear implant system 100 and/or any implementation thereof. While FIG. 6 illustrates exemplary operations according to embodiments described herein, other embodiments may omit, add to, reorder, and/or modify any of the operations shown in FIG. 6.

In operation 602, a controller operates in a therapeutic mode, by applying therapeutic electromagnetic pulses to a wound on a head of a recipient by way of a coil configured to be positioned over the wound, the therapeutic electromagnetic pulses configured to alleviate pain felt by the recipient while the wound heals. Operation 602 may be performed in any of the ways described herein.

In operation 604, the controller receives a command to operate in a cochlear implant interface mode in which the controller communicates by way of the coil with a cochlear implant implanted within the recipient. Operation 604 may be performed in any of the ways described herein.

In operation 606, the controller switches from the therapeutic mode to the cochlear implant interface mode. Operation 606 may be performed in any of the ways described herein.

Figure 7:
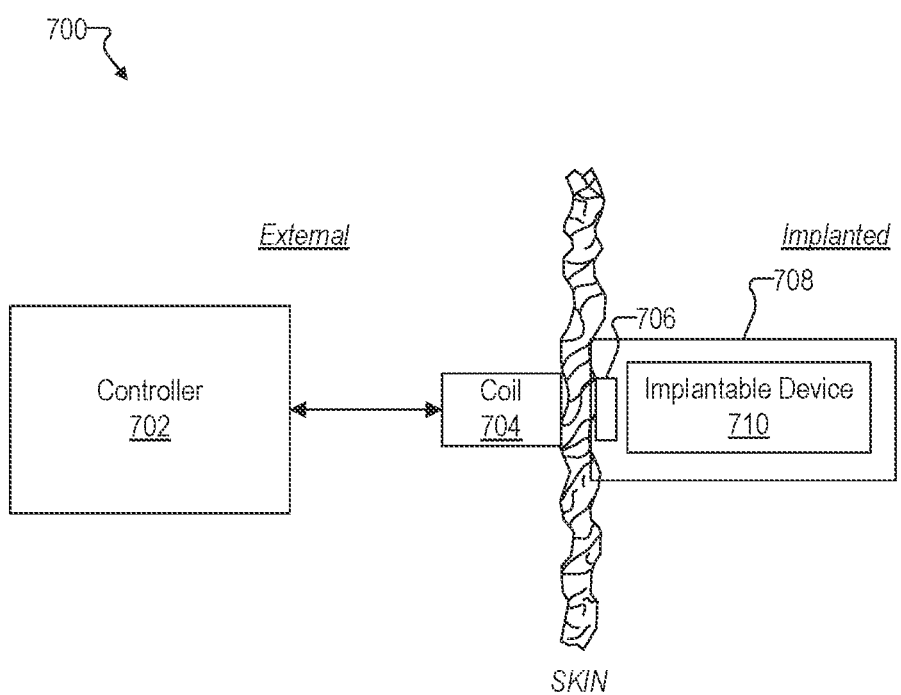
FIG. 7 illustrates an exemplary configuration according to principles described herein.

FIG. 7 illustrates another exemplary configuration 700 in which a controller 702 is configured to apply therapeutic electromagnetic pulses by way of a coil 704 to a wound. Controller 702 and coil 704 may be similar to any of the controllers and coils described herein. For example, controller 702 may include a power source and may be configured to be portable and operate autonomously. Coil 704 may be housed within any suitable housing (e.g., a headpiece and/or any other type of housing).

In configuration 700, coil 704 is configured to be positioned over a wound on a body and held in place on the body by a magnet 706 implanted within the body. The body may be a head and/or any other suitable body part of a person who has a wound. The wound may be the result of a medical procedure and/or caused by any other event or condition.

As shown, magnet 706 is included in an implantable assembly 708 that also includes an implantable device 710. Implantable device 708 may be implemented by any type of implantable medical device as may serve a particular implementation. For example, implantable device 708 may be implemented by an implantable stimulator, a cochlear implant, a pacemaker, and/or any other type of device configured to provide any type of therapeutic benefit to a recipient.

In some examples, controller 702 may be configured to selectively communicate with implantable device 710 by way of coil 704. For example, controller 702 may transmit data to and/or receive data from implantable device 710.

In some examples, controller 702 may be configured to detect a presence of implantable device 710 (e.g., when coil 704 is placed on the body). In response to detecting the presence of implantable device 710, controller 702 may initiate the therapeutic electromagnetic pulses and/or perform any other suitable operation.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
   a coil configured to be positioned over a wound on a body and held in place on the body by a magnet implanted within the body; and
   a controller communicatively coupled to the coil, the controller configured to apply therapeutic electromagnetic pulses by way of the coil to the wound.

2. The system of claim 1, further comprising an implantable assembly configured to be implanted within the body and including the magnet.

3. The system of claim 2, wherein the implantable assembly comprises an implantable device configured to communicate with the controller by way of the coil.

4. The system of claim 3, wherein:
   the controller is further configured to detect a presence of the implantable device; and
   initiate, in response to detecting the presence of the implantable device, the therapeutic electromagnetic pulses.

5. The system of claim 3, wherein the implantable device comprises an implantable stimulator, a pacemaker, or a cochlear implant.

6. The system of claim 1, wherein the controller is configured to selectively:
   operate in a therapeutic mode in which the controller applies the therapeutic electromagnetic pulses by way of the coil to the wound; and
   operate in a cochlear implant interface mode in which the controller communicates by way of the coil with a cochlear implant.

7. The system of claim 6, wherein the controller, while operating in the cochlear implant interface mode, is configured to:
   receive an audio signal; and
   wirelessly transmit a command to the cochlear implant, by way of the coil, to direct the cochlear implant to apply electrical stimulation representative of the audio signal received by the controller.

8. The system of claim 6, wherein the controller, while operating in the cochlear implant interface mode, is configured to wirelessly receive data from the cochlear implant by way of the coil.

9. The system of claim 8, wherein the controller is configured to use the data to guide a manner in which the controller operates in the cochlear implant interface mode.

10. The system of claim 1, wherein the coil is housed in a headpiece configured to be removably coupled to a housing configured to house the controller.

11. The system of claim 10, wherein the headpiece is configured to be positioned over a pinna of an ear of a recipient.

12. The system of claim 10, wherein the headpiece is configured to be magnetically held in place on a head of a recipient by an additional magnet of a cochlear implant.

13. The system of claim 10, wherein the headpiece is configured to be located in a wound covering or an article of clothing.

14. The system of claim 1, wherein the controller is configured to apply the therapeutic electromagnetic pulses in accordance with a therapeutic program stored in a memory of the controller, the therapeutic program specifying parameters of the therapeutic electromagnetic pulses.

15. The system of claim 14, wherein the parameters comprise at least one of an amplitude of the therapeutic electromagnetic pulses, a modulation depth of the therapeutic electromagnetic pulses, a pulse frequency of the therapeutic electromagnetic pulses, or a pulse duration of the therapeutic electromagnetic pulses.

16. The system of claim 14, wherein the controller is further configured to:

receive user input representative of a command to adjust a value for a parameter included in the parameters; and adjust, in response to receiving the user input, the value of the parameter.

17. The system of claim 16, wherein the user input is provided by way of a user input button on the controller.

18. The system of claim 14, wherein the controller is further configured to:

determine a placement context of the coil; and select the therapeutic program based on the determined placement context of the coil.

19. The system of claim 1, wherein the wound is created during an implant procedure in which a cochlear implant is implanted within a recipient.

20. The system of claim 1, wherein the therapeutic electromagnetic pulses are configured to alleviate pain felt by a recipient while the wound heals.

\* \* \* \* \*